United States Patent [19]

Barnett

[11] Patent Number: 5,394,736
[45] Date of Patent: Mar. 7, 1995

[54] GLYCOL TESTING UNIT

[76] Inventor: Buddy G. Barnett, Rte. 7 Box 698, Ruston, La. 71270-9123

[21] Appl. No.: 92,385

[22] Filed: Jul. 14, 1993

[51] Int. Cl.$^6$ .................... G01N 25/14; G01N 33/26
[52] U.S. Cl. .................... 73/31.07; 73/863.12; 73/863.86; 73/863.71; 374/54; 422/119
[58] Field of Search ........... 73/863.12, 863.21, 863.86, 73/864.51, 863.71, 864.63, 31.07, 64.56; 374/54; 422/119, 307; 436/142, 178

[56] References Cited

U.S. PATENT DOCUMENTS

| | | | |
|---|---|---|---|
| 2,720,788 | 10/1955 | Sibley | 73/64.56 X |
| 2,991,646 | 7/1961 | Wightman et al. | 73/31.07 |
| 3,022,659 | 2/1962 | Rochus et al. | 73/31.07 X |
| 3,429,186 | 2/1969 | Price et al. | 73/863.71 X |
| 3,504,549 | 4/1970 | Davis et al. | 73/863.71 X |
| 3,556,730 | 1/1971 | Mitacek | 73/863.86 X |
| 3,581,469 | 6/1971 | Davis et al. | 73/31.07 X |
| 3,930,414 | 1/1976 | Russell | 73/863.86 X |
| 3,950,136 | 4/1976 | Bellinga | 73/863.86 X |
| 4,191,541 | 3/1980 | Jenkins | 73/863.70 |
| 4,312,835 | 1/1982 | Zoltan | 422/70 |
| 4,335,620 | 6/1982 | Adams | 73/863.11 |
| 4,454,773 | 6/1984 | Brunner et al. | 73/863.86 X |
| 4,485,684 | 12/1984 | Weber | 73/863.12 |
| 4,488,887 | 12/1984 | Angel | 55/269 |
| 4,756,200 | 7/1988 | Ramsnor | 73/863.11 |

FOREIGN PATENT DOCUMENTS

| | | | |
|---|---|---|---|
| 17694 | 1/1987 | Japan | 73/31.07 |
| 179457 | 7/1990 | Japan | 73/64.56 |

OTHER PUBLICATIONS

Powder Technology (Switzerland), vol. 4, No. 6, Sep. 1971, pp. 293-301. "Equipment for Circulating Dense Gas/-Solid—Particle Suspensions for Process Development Studies"; P. J. Walton et al.

Primary Examiner—Thomas P. Noland
Attorney, Agent, or Firm—John M. Harrison

[57] ABSTRACT

A testing unit for testing the glycol reboiler effluent, waste gas, (effluent) concentration in glycol dehydrator reboilers, which unit includes an upward-standing separator device characterized by a shell and a tube extending through the shell, for receiving effluent from a glycol dehydrator reboiler. The effluent is routed from the reboiler upwardly in the tube and water entrained in the effluent is removed from the bottom of the tube by gravity. The effluent is then caused to flow through an orifice meter, where the effluent flow rate is measured and recorded by a Barton differential meter. A coolant is introduced into the testing unit on the shell side to cool the effluent stream and sample bombs are connected to the tube for sampling the stream to determine the chemical composition of the effluent.

20 Claims, 1 Drawing Sheet

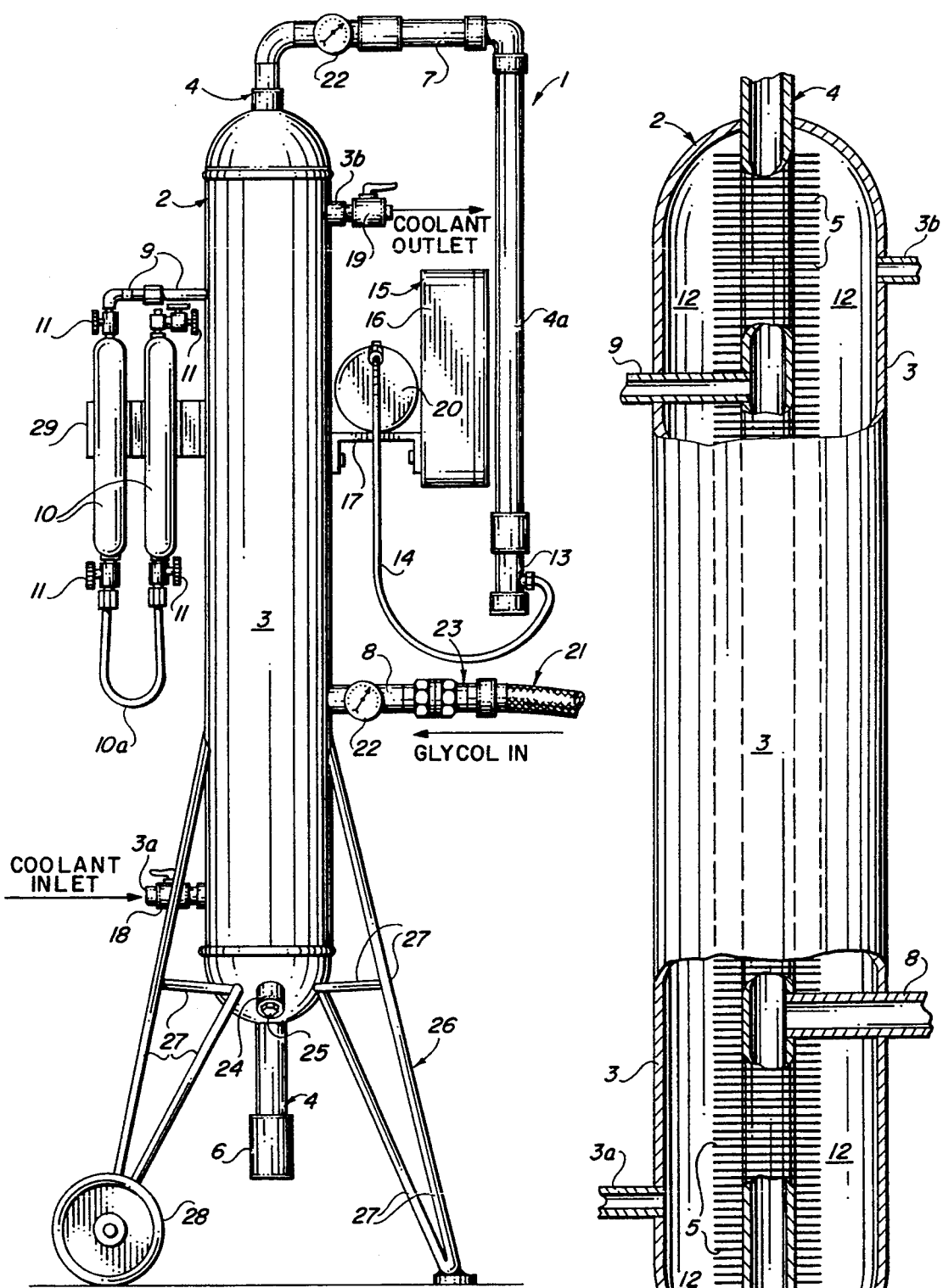

5,394,736

GLYCOL TESTING UNIT

BACKGROUND OF THE INVENTION

1. Field of the Invention

This invention relates to ethylene glycol (glycol) dehydrator reboilers and more particularly, to a portable apparatus for testing the flow rate and chemical composition of the reboiler effluent waste gas (effluent) stream from a glycol dehydrator reboiler or other glycol source. In a preferred embodiment the portable effluent testing unit is designed to determine the amount of reboiler effluent, waste gas which is released from a glycol dehydrator reboiler into the atmosphere. The portable effluent testing unit of this invention includes an upward-standing separator unit which is characterized by a shell portion fitted with a vertically-oriented internal tube that is optionally fitted with fins for cooling purposes. A cooling medium such as water is circulated through the shell and around the tube and fins to cool an effluent stream entering near the bottom of the tube and traveling upward to facilitate gravity removal of water entrained in the stream from the bottom of the unit. The effluent stream continues upward travel in the tube, where a sample nipple removes a portion of the stream for collection in a pair of bombs. The stream subsequently flows downwardly through a tube leg to an orifice meter, which operates to meter the flow rate of the effluent. The orifice meter is connected to a conventional Barton differential meter for registering the flow rate on a graph. In a preferred embodiment the testing unit is mounted on a frame fitted with wheels to enhance portability.

2. Description of the Prior Art

One of the problems inherent in operating ethylene glycol and other glycol dehydrator reboilers is that of exhausting the effluent stream to the atmosphere. In recent years, increasing emphasis has been placed on minimizing atmospheric pollution and it has therefore become important to determine the amount of effluent released to the atmosphere by these reboilers. Various types of testing apparatus have been used for this purpose, most of which are bulky, complex and difficult or impossible to transport.

Various types of testing apparatus are well known in the art for testing the chemical composition and flow rate of liquid and gaseous streams. A thermal control means for liquid chromatograph samples is detailed in U.S. Pat. No. 4,312,835, dated Jan. 26 1982, to Bart J. Zoltan, et al. The patent details a Peltier effect thermal control sample containment apparatus for an automatic sampling holding apparatus used in conjunction with a liquid chromatograph analysis. The apparatus provides for the cooling or heating of multiple liquid chromatography samples and the maintenance of these samples at specific temperatures for extended periods of time. U.S. Pat. No. 4,335,620, dated Jun. 22, 1982, to Wade J. Adams details a "Temperature Controlled Sample Carrier". The carrier includes a rotating sample rack having an array of upward-facing sample holes adjacent the rack periphery, for receiving sample vials and orbiting the sample vials sequentially past a sampling station. U.S. Pat. No. 4,485,684, dated Dec. 4, 1984, to Rudolph Weber, et al, details "Apparatus For Extracting and Analyzing Dust-Laden Gas Samples". The apparatus includes a gas extraction connection constructed in the form of a stilling chamber leading to an analyzer by means of a three-way valve, to which is connected a cleansing air connection. A time control device periodically interrupts the flow of gas to the analyzer and directs cleansing air through the extraction connection. U.S. Pat. No. 4,488,887, dated Dec. 18, 1984, to Anthony L. Angel, et al, details a "Cold Trap". The cold trap is designed to collect components of an aerosol stream and includes an elongated vessel provided with an aerosol stream inlet and outlet, a cooling jacket for subjecting a substantial portion of the walls of the vessel to temperatures below zero degrees Centigrade and a baffle assembly that includes multiple, spaced baffle plates which cooperate to present a tortuous path to the flow of the aerosol stream as it moves through the vessel. U.S. Pat. No. 4,756,200, dated Jul. 12, 1988, to Wolfgang Ramsner, et al, details a "Probe For Extracting Hot Sample Gas". The probe includes an inner tube for conducting a hot gas sample and a cooling jacket surrounding the inner tube. The heating element surrounds the heated inner tube and the inner tube is shielded from the cooling jacket by an interposed heat insulation.

It is an object of this invention to provide a portable glycol reboiler effluent, waste gas testing unit which is characterized by an upward-standing separator unit having a shell and an inner tube through which the glycol stream is directed. One or more sample bombs communicate with the tube for sampling the stream and an orifice meter is provided in the exit end of the tube and is connected to equipment for determining the flow rate of the stream.

Another object of this invention is to provide a new and improved glycol testing unit which includes a portable, upward-standing separator vessel fitted with a shell and an inner tube, which inner tube is fitted with fins for cooling and effluent stream directed thorugh the inner tube by means of a liquid circulated through the shell, a sample apparatus communicated with the tube for collecting effluent samples and determining the composition of the stream and an orifice meter mounted in the exit end of the tube and connected to a Barton differential meter for determining the flow rate of effluent through the tube.

Another object of the invention is to provide a new and improved, portable glycol effluent testing unit for determining the volume and chemical composition of ethylene glycol or other glycol composition effluent released from a glycol dehydrator reboiler, which testing unit is characterized by an upward-standing shell fitted with wheels to enhance portability and having an internal tube to define an annulus through which a cooling medium is circulated, a sample apparatus connected to the tube for collecting a sample(s) of the effluent stream and determining the chemical composition of the stream and an orifice meter attached to the downwardly-extending exit end of the tube and connected to a Barton differential meter for determining the flow rate of the stream through the testing unit.

SUMMARY OF THE INVENTION

These and other objects of the invention are provided in a new and improved, portable glycol testing unit for determining the volume and chemical composition of effluent exhausted to the atmosphere from a glycol dehydrator reboiler, which unit is characterized by an upward-standing separator unit mounted on a stand fitted with wheels for portability and characterized by a shell with an inner tube extending through the shell to define an annulus for receiving a cooling stream to cool effluent which is routed from the glycol dehydrator reboiler upwardly through the tube. Water entrained in the stream is separated by gravity from the effluent at the bottom of the tube and a pair of sample bombs communicate with the tube for collecting samples of the effluent stream and determining the concentration and chemical composition of the stream. An orifice meter is provided on a downwardly-extending leg of the tube and is connected to a Barton differential meter for determining the flow rate of the stream.

BRIEF DESCRIPTION OF THE DRAWING

The invention will be better understood by reference to the accompanying drawing, wherein:

FIG. 1 is a side view of a preferred embodiment of the glycol testing unit of this invention; and FIG. 2 is a side view, partially in section, of the separator unit of the glycol testing unit illustrated in FIG. 1.

DESCRIPTION OF THE PREFERRED EMBODIMENTS

Referring to FIGS. 1 and 2 of the drawing, the glycol testing unit of this invention is generally illustrated by reference numeral 1. The glycol testing unit 1 is characterized by a vertically-oriented separator unit 2, having a shell 3 fitted with a shell drain 24 and drain plug 25, as well as a coolant inlet 3a and coolant inlet valve 18 at the bottom thereof. A coolant exit 3b and coolant exit valve 19 are provided at the top of the shell and a tube 4 extends vertically through the center of the shell 3, to define an annulus 12. In a most preferred embodiment of the invention, the tube 4 is characterized by a multiple tube fins 5 extending within the annulus 12, to facilitate cooling of an effluent stream routed upwardly through the tube 4 by circulation of a cooling fluid such as chilled water through the annulus 12 by connection to the coolant inlet 3a and the coolant exit 3b. A tube drain 6 is provided at the bottom end of the tube 4 and extends through the shell 3 to drain entrained water separated from the cooled glycol effluent stream by gravity as the stream travels upwardly from an entrance point in the effluent inlet line 8. The effluent stream extends upwardly through the tube 4 and exits through the horizontal tube outlet line 7, which curves downwardly to a vertical tube leg 4a, where an orifice meter 13 is mounted on the end thereof, as illustrated in FIG. 1. A sample collection nipple 9 extends through the shell 3 and annulus 12, into the tube 4 to communicate with the stream flowing upwardly through the tube 4. The sample collection nipple 9 is fitted to a sample valve 11 to control the flow of effluent from the tube 4 through the sample collection nipple 9 and into the sample bombs 10, mounted on a bracket 29, connected by a bomb connecting line 10a and controlled by sample valves 11, to collect samples from the effluent stream for analysis. An impulse line 14 extends from the orifice meter 13 to the meter bellows 20 of a Barton differential meter 15, characterized by a meter housing 16 mounted on a meter support 17, secured to the shell 3 of the separator unit 2. A graph (not illustrated) is fitted in the meter housing 16 and a pair of pins (not illustrated) record the flow rate of the effluent downwardly through the vertical leg of the tube 4 and the orifice meter 13 and exhausted to the atmosphere. The glycol testing unit 1 is connected to a glycol dehydrator reboiler (not illustrated) in conventional fashion by means of an effluent inlet hose 21, which is attached to the effluent inlet line 8 by means of a hose coupling 23. Effluent inlet and outlet thermometers 22 are provided in the effluent inlet line 8 and tube outlet line 7 to determine the incoming and outgoing temperature of the effluent, respectfully.

Referring again to FIG. 1 of the drawing, in a most preferred embodiment of the invention the separator unit 2 is supported by a shell support 26, attached to the shell 3 and characterized by support members 27, attached to the shell 3 by welding and fitted with a pair of wheels 28, to enhance portability.

It will be appreciated from a consideration of the glycol testing unit 1 of this invention that the device can be easily loaded into a pickup truck or other carrier and transported to any location where glycol dehydrator reboilers may be tested for glycol effluent emissions. The glycol testing unit 1 can be set up in the pickup truck and the effluent inlet hose 21 connected to the glycol dehydrator reboiler to facilitate passage of an effluent stream through the tube 4 for receiving a sample or samples and analyzing not only the chemical content of the effluent stream, but also the flow rate of the stream. Accordingly, once the effluent inlet hose 21 has been connected to the glycol dehydrator reboiler and to the separator unit 2, a steady-state flow condition is established, with effluent flowing upwardly through the tube 4 and subsequently downwardly through the tube leg 4a and the orifice meter 13, to the atmosphere. Water is continually drained by gravity from the stream through the tube drain 6. Effluent samples may be collected by manipulating the sample valve 11 which controls the flow of effluent from the tube 4 into the sample bombs 10 and the sample bombs 10 can be removed from the sample collection nipple 9 for insertion in a gas phase chromatograph or other instrument (not illustrated) to determine the chemical composition of the effluent stream. Furthermore, the flow rate of the stream is measured by the Barton differential meter as the effluent is exhausted to the atmosphere through the orifice meter 13.

It will be appreciated that the glycol testing unit of this invention offers a simple, readily available, economical and portable device for testing ethylene glycol and other glycol derivative effluent flow rates and compositions from glycol dehydrator reboilers. Specifically, the amount of effluent emitted to the atmosphere by the glycol dehydrator reboilers may be determined, as well as the chemical composition of the effluent, in order to evaluate the polluting effects of effluent discharge.

While the preferred embodiments of the invention have been described above, it will be recognized by those skilled in the art that various other modifications may be made in the invention without departing from the spirit and scope thereof.

Having described my invention with the particularity set forth above, what is claimed is:

1. A glycol testing unit comprising a separator unit having a tube extending therethrough to define a shell having a shell side surrounding a selected length of said tube; an effluent inlet line communicating with said tube for introducing glycol effluent into said tube; an orifice meter provided in said tube downstream from said effluent inlet line for metering effluent flowing through said tube; and pressure-operated recording means provided in pressure communication with said orifice meter for receiving pressure impulses from said orifice meter and recording the flow rate of effluent through said orifice meter.

2. The glycol testing unit of claim 1 comprising sample container means communicating with said tube for collecting samples of the effluent.

3. The glycol testing unit of claim 2 wherein said sample container means comprises a first sample bomb communicating with said tube and first valve means provided on one end of said first sample bomb for controlling the flow of effluent from said tube into said first sample bomb; a second sample bomb communicating with said first sample bomb; second valve means provided on the opposite end of said first sample bomb from said one end for controlling the flow of effluent from said first sample bomb into said second sample bomb; third valve means provided on one end of said second sample bomb for controlling the flow of effluent from said first sample bomb into said second sample bomb; and third valve means provided on the opposite end of said second sample bomb from said one end for controlling the flow of effluent from said second sample bomb.

4. The glycol testing unit of claim 3 comprising cooling fluid inlet and outlet lines communicating with said shell side of said separator unit for introducing a cooling fluid into said shell side and cooling said selected length of said tube and the effluent.

5. The glycol testing unit of claim 4 comprising a plurality of fins provided on said tube, said fins extending into said shell side of said separator unit for extending the surface area of said selected length of said tube exposed to the cooling fluid.

6. The glycol testing unit of claim 5 comprising a shell support carried by said shell for supporting said glycol testing unit in substantially vertical orientation and at least one wheel provided in said shell support for rolling said glycol testing unit.

7. The glycol testing unit of claim 1 comprising cooling fluid inlet and outlet lines communicating with said shell side of said separator unit for introducing a cooling fluid into said shell side and cooling said selected length of said tube and the effluent.

8. The glycol testing unit of claim 7 comprising a plurality of fins provided on said tube, said fins extending into said shell side of said separator unit for extending the surface area of said selected length of said tube exposed to the cooling fluid.

9. The glycol testing unit of claim 7 comprising sample container means communicating with said tube for collecting samples of the effluent.

10. The glycol testing unit of claim 9 comprising a plurality of fins provided on said tube, said fins extending into said shell side of said separator unit for extending the surface area of said selected length of said tube exposed to the cooling fluid.

11. The glycol testing unit of claim 1 comprising a shell support carried by said shell for supporting said glycol testing unit in substantially vertical orientation.

12. The glycol testing unit of claim 11 comprising at least one wheel provided in said shell support for rolling said glycol testing unit.

13. The glycol testing unit of claim 12 comprising sample container means communicating with said tube for collecting samples of the effluent.

14. The glycol testing unit of claim 12 comprising cooling fluid inlet and outlet lines communicating with said shell side of said separator unit for introducing a cooling fluid into said shell side and cooling said selected length of said tube and the effluent.

15. The glycol testing unit of claim 12 comprising:
(a) sample container means communicating with said tube for collecting samples of the effluent; and
(b) cooling fluid inlet and outlet lines communicating with said shell side of said separator unit for introducing a cooling fluid into said shell side and cooling said selected length of said tube and the effluent.

16. The glycol testing unit of claim 15 comprising a plurality of fins provided on said tube, said fins extending into said shell side of said separator unit for extending the surface area of said selected length of said tube exposed to the cooling fluid.

17. A glycol testing unit for determining the volume of effluent escaping from a glycol reboiler, comprising a separator unit characterized by a substantially vertically-oriented shell; a tube extending longitudinally through said shell to define an annulus between said tube and said shell; an effluent inlet line provided in fluid communication with said tube for introducing effluent from the glycol reboiler upwardly into said tube; at least one sample container carried by said shell and communicating with said tube for receiving a sample of effluent from said tube; an orifice meter provided in said tube downstream from said glycol inlet line for metering effluent flowing through said tube; pressure-operated recording means provided in pressure communication with said orifice meter for receiving pressure impulses from said orifice meter and recording the flow rate of effluent through said orifice meter; and cooling fluid inlet and outlet lines communicating with said annulus in said separator unit for circulating a cooling fluid through said annulus and cooling said effluent.

18. The glycol testing unit of claim 17 comprising a shell support carried by said shell for supporting said glycol testing unit in substantially vertical orientation and at least one wheel provided in said shell support for rolling said glycol testing unit.

19. The glycol testing unit of claim 17 comprising a plurality of fins provided on said tube, said fins extending into said annulus of said separator unit for extending the surface area of said selected length of said tube exposed to the cooling fluid.

20. The glycol testing unit of claim 17 wherein said at least one sample container comprises a first sample bomb communicating with said tube and first valve means provided on one end of said first sample bomb for controlling the flow of effluent from said tube into said first sample bomb; a second sample bomb communicating with said first sample bomb; second valve means provided on the opposite end of said first sample bomb from said one end for controlling the flow of effluent from said first sample bomb into said second sample bomb; third valve means provided on one end of said second sample bomb for controlling the flow of effluent from said first sample bomb into said second sample bomb; and third valve means provided on the opposite end of said second sample bomb from said one end for controlling the flow of effluent from said second sample bomb, and comprising:
(a) a shell support carried by said shell for supporting said glycol testing unit in substantially vertical orientation and a pair of wheels provided in said shell support for rolling said glycol testing unit; and
(b) a plurality of fins provided on said tube, said fins extending into said shell side of said separator unit for extending the surface area of said selected length of said tube exposed to the cooling fluid.

* * * * *